United States Patent [19]

Svensson et al.

[11] 4,058,368
[45] Nov. 15, 1977

[54] HYDROGEN DETECTOR

[75] Inventors: Christer Martinus Svensson, Goteborg; Leif Sigurd Lundkvist, Angered; Kurt Ingemar Lundstrom; Madurai Somanathan Shivaraman, both of Goteborg, all of Sweden

[73] Assignee: Semiconductor Sensors, Inc., Cupertino, Calif.

[21] Appl. No.: 611,404

[22] Filed: Sept. 9, 1975

[30] Foreign Application Priority Data

Sept. 9, 1974 Sweden .................................. 7411342

[51] Int. Cl.$^2$ ...................... G01N 27/12; G01N 31/06
[52] U.S. Cl. ...................................... 23/254 E; 73/23; 324/71 SN; 357/23; 357/25
[58] Field of Search ............ 23/254 E, 255 E, 257 E; 357/23, 25; 324/71 SN; 73/23

[56] References Cited

U.S. PATENT DOCUMENTS

| | | | |
|---|---|---|---|
| 2,975,362 | 3/1961 | Jacobson | 324/71 SN |
| 3,428,892 | 2/1969 | Meinhard | 324/71 SN ED |
| 3,831,432 | 8/1974 | Cox | 73/23 |

Primary Examiner—Robert M. Reese
Attorney, Agent, or Firm—Warren M. Becker

[57] ABSTRACT

A device for the detection of hydrogen comprising a semiconductor, a metal electrode and an insulator situated between the semiconductor and the electrode. The metal electrode is made of palladium, nickel, platinum or an alloy containing at least 20% palladium by atomic weight. In one embodiment, the device is a field-effect transistor. Means are also provided for heating the device for improving its response time.

6 Claims, 8 Drawing Figures

HYDROGEN DETECTOR

BACKGROUND OF THE INVENTION

The present invention concerns a device for detection of hydrogen in the form of hydrogen gas, atomic hydrogen or certain gaseous hydrogen compounds, for example ammonia.

A disadvantage which is common to all prior-art gas detectors of relatively simple construction is their limited selectivity — i.e., that they respond to several kinds of gases. For example, some detectors are sensitive to all combustible gases (hydrocarbons, alcohols, etc.). Because of the large number of gases that give positive readings in these detectors, such detectors are difficult to use.

SUMMARY OF THE INVENTION

The present invention provides a detector which, in spite of its simple construction, makes it possible to achieve quick and reliable detection of hydrogen in the form of hydrogen gas, atomic hydrogen or hydrogen compounds. The invention is based on the knowledge that the platinum metals, especially palladium, but also platinum and nickel, are able to dissociate hydrogen gas, to dissolve and allow penetration of hydrogen and to adsorb hydrogen in their surface layers. This specific property of the metals mentioned is used in connection with semiconductors having a field effect structure, for example field-effect transistors, the threshold voltage of which is dependent on the emissive power of their gate electrodes.

The device according to the present invention thus is characterized by a semiconductor, a metal electrode and an insulator situated between the conductor and the electrode. The metal electrode is made of palladium, nickel, platinum or an alloy containing at least 20% palladium by atomic weight.

In accordance with a further development of this invention, the device is a field-effect transistor, wherein the gate electrode is made of palladium, nickel, platinum or an alloy containing at least 20% palladium by atomic weight.

When a device constructed as mentioned above is exposed to hydrogen, some of the hydrogen will be adsorbed on the surface of the metal electrode or gate electrode, diffuse through the electrode and be adsorbed on the electrode surface facing the insulator. This process affects the emissive power of this surface, and as a consequence the electrical function of the semiconductor or transistor will change, and this effect is used to detect the presence of hydrogen.

DESCRIPTION OF THE DRAWINGS

The above and other objects, features and advantages of the invention will be apparent in the following detailed description and accompanying drawings in which.

DETAILED DESCRIPTION

Figure 1:
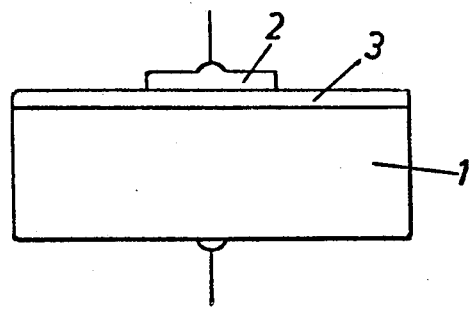
FIG. 1 shows a semiconductor having a field-effect structure.

Referring to FIG. 1, the most simple embodiment of the device in accordance with the invention comprises a semiconductor 1 and a metal electrode 2 with an insulator 3 arranged intermediate the conductor and the electrode. The metal electrode is preferably made of palladium or a metal alloy having a palladium content of at least 20% by atomic weight. It is also possible to make the metal electrode 2 of nickel or platinum, but in this case the sensitivity of the device is less good.

Figure 3:
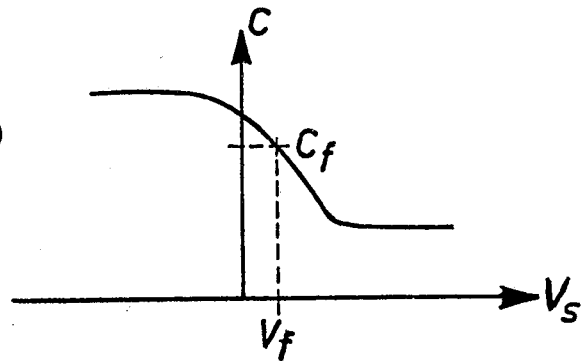
FIGS. 3 and 4 are electrical curve charts.

FIG. 3 shows a curve chart illustrating the MOS-capacitance C of the device as a function of a gate voltage $V_s$ applied to the device. When the device is exposed to hydrogen, its electrical properties will change — i.e., the so-called flatband voltage $V_f$ will change and as a result thereof the capacitance curve will move in the diagram. The point $C_f$ thus will move, which can be used to detect hydrogen.

Figure 2:
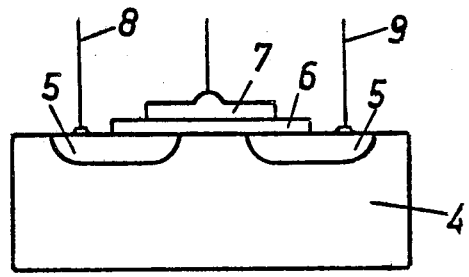
FIG. 2 shows a field-effect transistor.

FIG. 2 shows a field-effect transistor which is made of a silicon semiconductor of p-type and which has two silicon layers 5 of n-type integrated thereinto. Furthermore, the transistor comprises an insulating layer 6 in contact with the semiconductor layers 4 and 5, a gate electrode 7 of palladium, nickel, platinum or a palladium alloy, and an emitter electrode 8 and a collector electrode 9.

Figure 4:
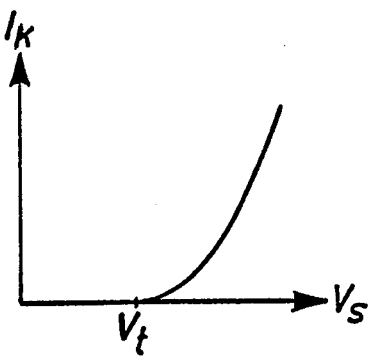

When this field-effect transistor is exposed to hydrogen, the emissive power of the gate electrode 7 will change and with it the threshold voltage of the transistor. FIG. 4 shows a curve chart of the collector current $I_K$ as a function of the gate voltage $V_s$. Due to the influence of hydrogen on the threshold voltage, the point $V_t$ will move, which is made use of to detect hydrogen. For instance, one may measure $I_K$ and the presence of hydrogen thus is recorded on an ammeter.

Figure 5:
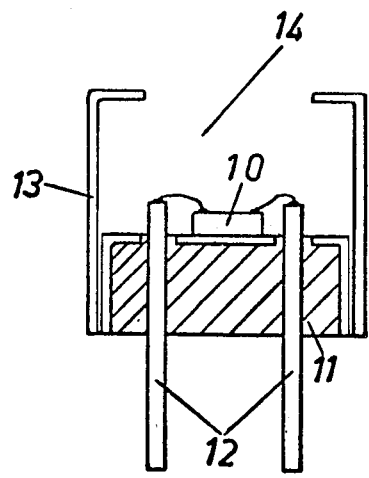
FIG. 5 illustrates one embodiment of the device in accordance with the invention.
Figure 6:
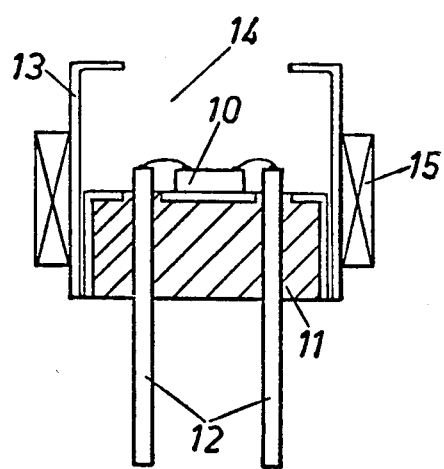
FIG. 6 illustrates another embodiment of the device.
Figure 7:
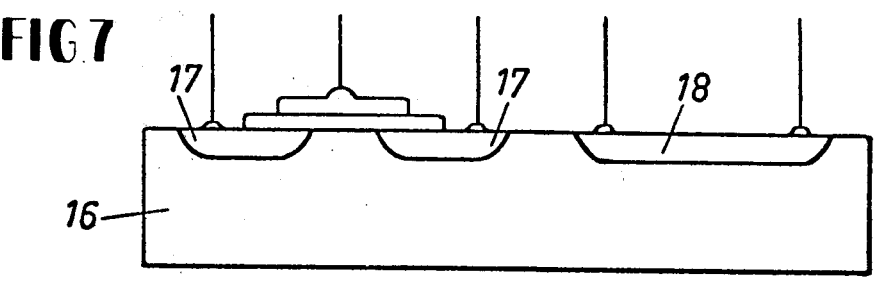
FIG. 7 illustrates a third embodiment.

FIGS. 5–7 show various arrangements of practical applications of field-effect transistors as hydrogen detectors. The transistor 10 rests on a header 11 of glass or plastics and is connected in the conventional manner to conductors 12 and enclosed in a cover 13. As appears from FIGS. 5 and 6, this cover must have an opening 14, making it possible for the gate of the transistor to record the presence of hydrogen.

Figure 8:
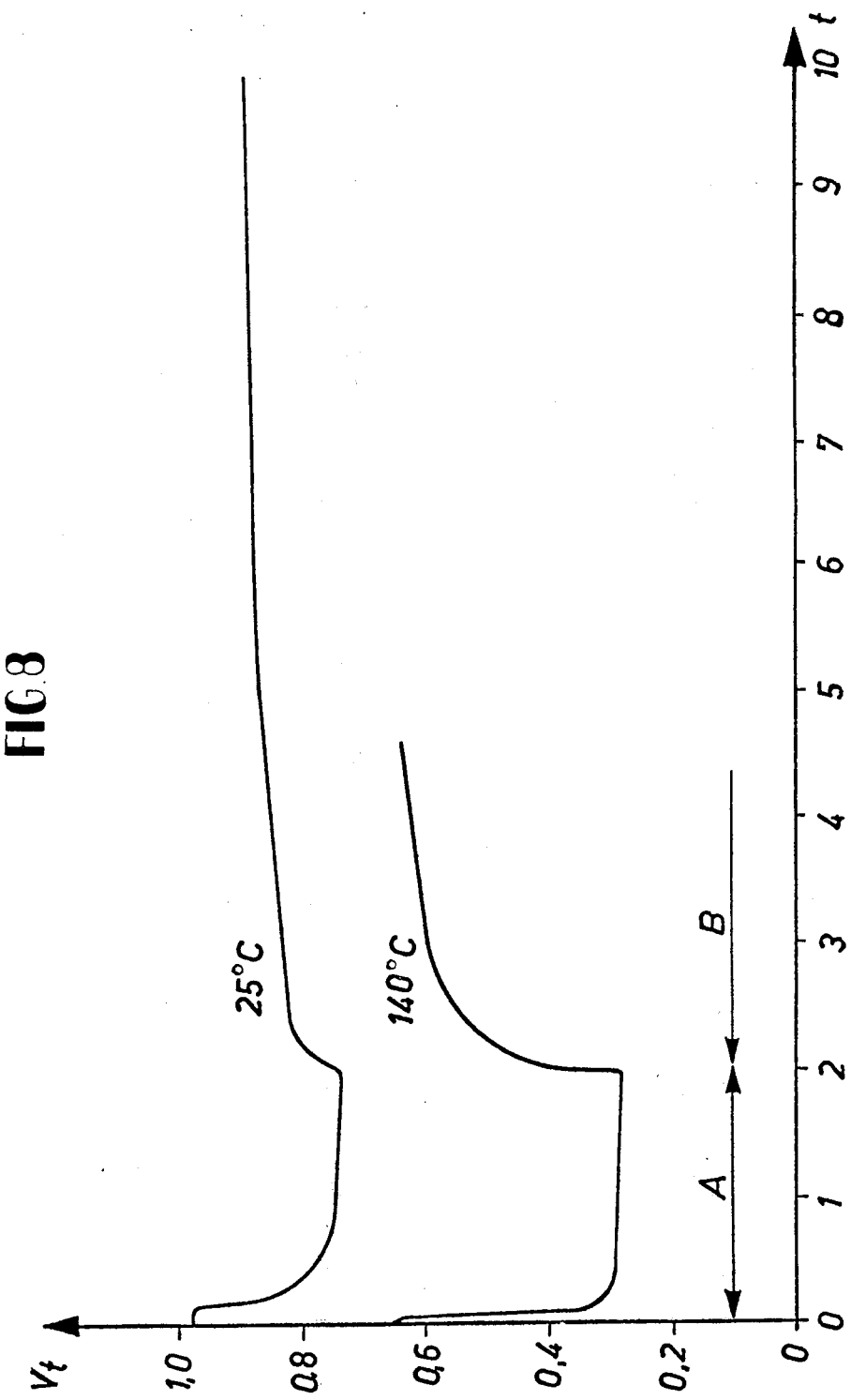
FIG. 8 is a further curve chart.

In accordance with the embodiment of FIG. 6, a heater means 15 is arranged around the device, whereby the device may be heated to temperatures of between 50° C and 250° C during the hydrogen detection process. The advantage of such heating is most simply explained with reference to FIG. 8 in which are shown two curve charts with the threshold voltage $V_t$ as a function of time expressed in minutes in an n-channel field-effect transistor of silicon having about $20 \times 10^{-9}$ meters thick layer of silicon dioxide as the gate insulation and about $20 \times 10^{-9}$ meters thick layer of palladium as the gate electrode. The device is exposed to air containing 5% of hydrogen gas, which is removed from the air after a couple of minutes. When the transistor is heated to a temperature of 25° C, the threshold voltage decreases, as illustrated, to a lower value and remains at this level over the period A during which the transistor is exposed to the hydrogen gas. As soon as the hydrogen gas is removed from the air, the threshold voltage will again rise over a period B which is not strictly determined and will finally return to its initial value.

With the transistor heated to 140° C, the decrease of the threshold voltage will be faster and larger than in the first case upon exposure to hydrogen, and, after removal of the hydrogen, the voltage increase toward the initial value will also occur faster. Heating of the device thus improves the reactional speed and sensitivity of the device, thus making it more reliable for hydrogen detection purposes.

FIG. 7 shows, on an enlarged scale, a modified embodiment of the device in FIG. 6. The semiconductor 16 is made of silicon plate of p-type. In addition to the silicon layer 17 of the transistor, the heater means 18 is arranged in the silicon plate in the form of an integrated circuit. The material of the heater means 18 preferably also is n-type silicon.

Owing to this structure of the device, the energy requirements for the heating are reduced.

The device in accordance with the present invention may find application within several technical fields. It may be used as a leak detector in systems using hydrogen gas (city gas, column gas, etc.), as a leak detector in other systems, the hydrogen gas then being used as a tracer, or as an alarm detector to indicate the presence of hydrogen within industries where hydrogen or gases containing hydrogen are used (such as petrochemical industries, electrochemical industries, gasworks) for the purpose of preventing gas explosions. The device may also be used to measure the partial pressure of hydrogen gas.

The invention is not limited to these embodiments shown and described in the aforegoing but various alterations and modifications are possible within the scope of the appending claims. Various alloys for the material of the metal or gate electrodes are, of course, possible. The structure of the device incorporating the field-effect transistor and heater means may also be effected in several ways.

What is claimed is:

1. An improved device for detection of hydrogen in the form of hydrogen gas, atomic hydrogen or certain gaseous hydrogen compounds, including ammonia, the improvement comprising a semiconductor, a metal electrode and an insulating layer positioned intermediate said semiconductor and said electrode, said metal electrode made from palladium, nickel, platinum or an alloy containing at least 20% palladium by atomic weight.

2. An improved device according to claim 1, wherein said device is a field-effect transistor, the gate electrode of said transistor made from palladium, nickel, platinum or an alloy containing at least 20% palladium by atomic weight.

3. An improved device according to claim 2, wherein means are provided to heat the device to temperatures ranging between 50° and 250° C.

4. An improved device according to claim 3, wherein said heater means is a part of said semiconductor in the form of an integrated circuit.

5. An improved device according to claim 1 wherein means are provided to heat the device to temperatures ranging between 50° and 250° C.

6. An improved device according to claim 5, wherein said heater means is a part of said semiconductor in the form of an integrated circuit.

* * * * *